United States Patent [19]

Wright

[11] Patent Number: 4,615,210
[45] Date of Patent: Oct. 7, 1986

[54] VISCOMETER SYSTEM

[75] Inventor: Donald G. Wright, Rockville Centre, N.Y.

[73] Assignee: Adelphi Center For Energy Studies, Garden City, N.Y.

[21] Appl. No.: 729,866

[22] Filed: May 2, 1985

[51] Int. Cl.[4] .............................................. G01N 11/04
[52] U.S. Cl. ....................................................... 73/55
[58] Field of Search ...................... 73/55, 56; 137/329.3

[56] References Cited

U.S. PATENT DOCUMENTS 2,022,578  11/1935  Thomas ..................................... 73/55
2,091,222   8/1937  Thomas ..................................... 73/55

FOREIGN PATENT DOCUMENTS 201050  10/1889  France ..................................... 73/55

Primary Examiner—Stewart J. Levy
Assistant Examiner—Joseph W. Roskos
Attorney, Agent, or Firm—Wyatt, Gerber Shoup, Scobey and Badie

[57] ABSTRACT

A viscometer system to measure the viscosity at high shear rates of thick liquids such as coal slurries includes a vessel to contain the liquid and a nitrogen pressure source connected to the vessel to apply nitrogen pressure to the liquid. A valve operated by a pneumatic actuator, preferably controlled by a computer, controls the orifice through which the liquid flows. The valve includes a ball member having a bore therethrough which bore, upon actuation of the valve, is aligned with the input and output orifices of the valve block to permit flow of the liquid.

5 Claims, 4 Drawing Figures

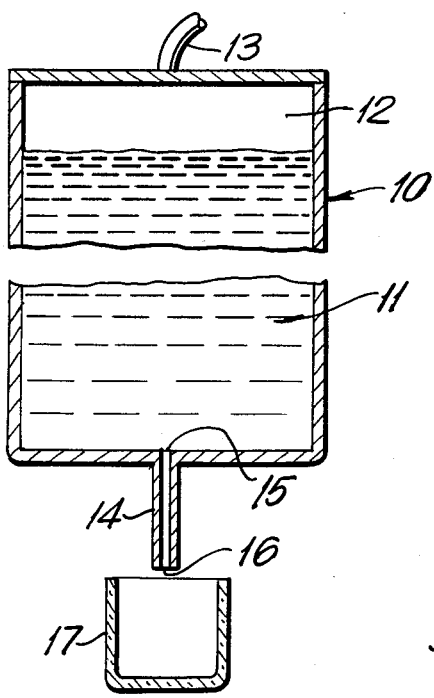
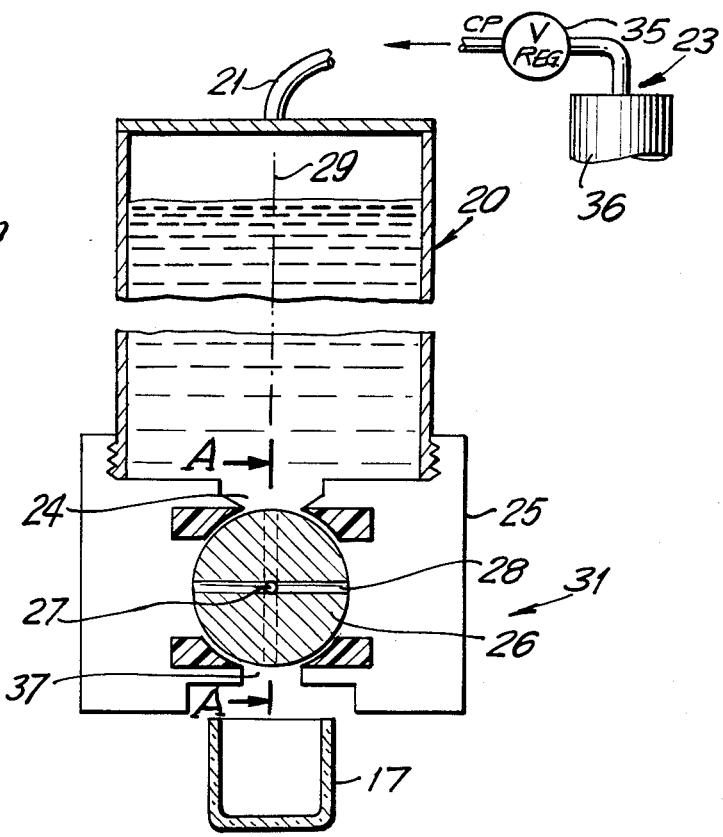
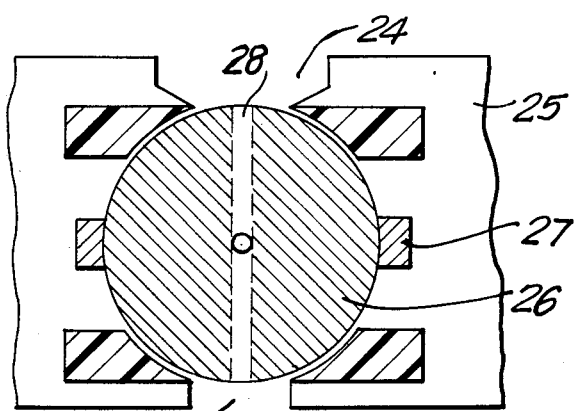
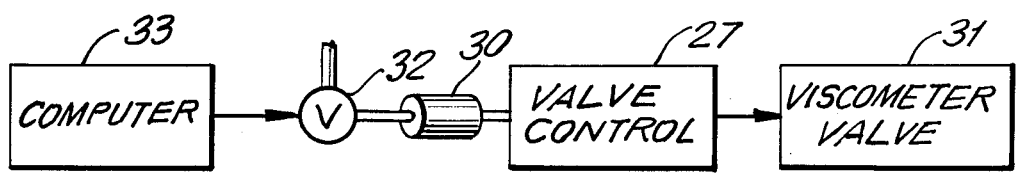

4,615,210

VISCOMETER SYSTEM

BACKGROUND OF THE INVENTION

The present invention relates to measurement instruments and more particularly to a viscometer for measuring the viscosity at high shear rates, of a thick liquid.

The measurement of the viscosity of a thick liquid, using presently commercially available instruments, presents various problems. The measurement process may be time-consuming and difficult to integrate into an automatic control system. The present methods of viscosity measurement depend upon the training, skill and care of the person performing the measurement. In certain viscosity measurement systems pressure must be applied to one face of the liquid, in a supply vessel, so that a sample may be drawn off and weighed. However, the pressure may be uneven and the supply vessel may drip before or after the liquid sample is drawn.

These problems are particularly acute when the liquid is a coal slurry, such as a coal-in-oil or coal-in-water slurry, in which microscopic sized bits of coal are suspended in a thick oil or water. In a typical slurry the coal particles are less than 75 microns in diameter (85% of particles). The viscosity of the slurry should be frequently measured in order to burn the slurry at its best combustion efficiency and as a quality control measure in the manufacture, storage and purchase of the coal slurry.

The viscosity of a viscous liquid may be derived from the formula applicable to its flow in a uniform tube:

$$\eta = D\,(\Delta P/Ql)$$

where $\eta$ is viscosity, P is pressure, Q is flow rate and l is length of tube.

The presently commercially available viscometer to measure slurries suffers from inaccuracies because the pressure (P) is not uniform from one measurement to another and because the flow rate is not uniform because of dripping of the sample.

OBJECTIVES AND FEATURES OF THE INVENTION

It is an objective of the present invention to provide a viscometer instrument to measure the viscosity of thick liquids, such as coal slurries, and which will provide a relatively accurate measurement of the viscosity of the liquid.

It is a further objective of the present invention to provide such a visometer that may be used without the accuracy of the measurement depending upon the skill and care of the operator.

It is a further objective of the present invention to provide such a viscometer that may be integrated into a computer-based automatic control system in which the viscosity measurements are taken and recorded automatically and in which the results of the viscosity measurements are utilized as control parameters.

It is a feature of the present invention to provide a viscometer system to measure the viscosity of thick liquids such as coal slurries. The viscometer system includes a vessel, such as a cylindrical metal tube, adapted to contain the liquid. Pressure means, such as a pressurized nitrogen or other inert gas cylinder, is connected to the vessel to selectively apply pressure to the liquid. The pressure forces the liquid from the vessel. The vessel has an orifice means to permit the liquid to flow from the vessel.

A valve means controls the flow of the liquid. The valve means includes a valve block, a ball rotatably mounted in the valve block with a bore therethrough, pivot means to rotatably mount the ball in the valve block, and control means to rotate the ball and thereby operate the valve means.

It is a further feature of the present invention that the viscometer system includes automatic means to operate the control means under computer program command. Such automatic means preferably includes a pneumatic cylinder and piston connected to the valve block control means, a pneumatic valve connected to and controlling the pneumatic cylinder, and a programmed digital computer connected to and controlling the pneumatic valve.

BRIEF DESCRIPTION OF THE DRAWINGS

Other objectives and features of the present invention will be apparent from the following detailed description, taken in conjunction with the accompanying drawings.

In the drawings:

FIG. 1 is a side cross-sectional view of a prior art viscometer;

FIG. 2 is a side cross-sectional view of the viscometer of the present invention;

FIG. 3 is an enlarged cross-sectional view taken along line A—A of FIG. 2; and

FIG. 4 is a block schematic diagram of the viscometer system of the present invention.

DETAILED DESCRIPTION OF THE INVENTION

As shown in FIG. 1, the prior art viscometer includes a pressure vessel 10 which is a metal cylindrical tube. The vessel 10 is vertically aligned. The liquid 11, for example, a coal slurry, is poured into the vessel 10, leaving a nitrogen gap 12 above the level of the liquid 11. A nitrogen tube 13, at the top of the vessel 10, leads a source of nitrogen pressure, for example, a pressurized nitrogen cylinder.

A measurement tube 14, having a predetermined length, has its top (entry) orifice 15 within the vessel 10 and its bottom (exit) orifice 16 below the vessel 10.

A container 17 (beaker) is positioned beneath orifice 16 to receive the liquid which flows from the orifice. The container, after it receives the liquid, is weighed using an accurate scale to determine how much liquid has flowed through tube 14 in the selected time period.

In one method of using the viscometer of FIG. 1, an operator places his finger over orifice 16 to act as a valve, and turns on the pressure. He looks at his stop watch, removes his finger, permits the liquid to flow for a selected time period, for example, one minute, and then replaces his finger on the orifice 16 to stop the flow and vents the pressure while measuring time. He will then weigh the container 17 and calculate the viscosity of the liquid.

The viscometer of the present invention is shown in FIGS. 2-4. It includes a cylindrical tubular vessel 20, preferaby of metal, which is vertically aligned. A tube 21, at the top of the vessel 20, is connected to a source of regulated air pressure 23, preferably a cylinder of pressurized air and a pressure regulator.

The vessel 20, at its bottom, has a conical orifice 24 which leads to a valve block 25. The valve block 25, which is part of valve 31, has an internal ball 26, for example, 2½ inches in diameter, which pivots (rotates) about its shaft 27 one-quarter of a turn (90°). The shaft 27 is perpendicular to the imaginary vertical axis 29 of the vessel 20 and, as seen in FIG. 2, it is vertical to that Figure. The ball 26 has a bore 28 through its diameter.

A container 17 is positioned beneath the valve block 25. This container can be attached to a load cell to automatically give weight of sample collected.

The shaft 27 is pivoted 90° to open the valve by a pneumatic cylinder 30 having an actuator (piston). The cylinder 30 is operated by an electro-pneumatic valve 32 and the valve 32 is controlled by the computer 33, see FIG. 4.

In operation, the operator will vary the nitrogen pressure regulator 35 to set predetermined nitrogen pressures which are sufficient to force the liquid to flow from the vessel 20, for example, 20 to 100 pounds per square inch. Preferably, the pressure regulator will be automatically adjusted by the computer 33. The pressure regulator 35, which is connected to the pressurized air cylinder 36, will conduct pressurized gas through the tube 21 to the vessel 20. When the system is manually operated, the operator will operate the valve 32 to control the piston 30. The piston 30 operates the valve control shaft 27.

As shown in FIG. 3, the ball 26 has an opposite and outwardly extending shaft 27, which is rotated 90° to open the valve.

The closed position of the valve 31 is shown in FIGS. 2 and 3. In the closed position the solid line shows the bore 28 as being horizontal. In the operated position, shown in dash lines in FIGS. 2 and 3, the bore 28 is vertical and aligned with the valve seat of the valve block. Preferably, as shown, the inlet orifice 24 is tapered. Both of the orifices 24 and 37 have valve gaskets, for example, P.T.F.E. (DuPont brand "Teflon") to prevent leakage.

What is claimed is:

1. A viscometer system to measure the viscosity of thick liquids such as coal slurries, the viscometer system including:
    a gas-tight vessel to contain the liquid;
    gas pressure means connected to the vessel to selectively apply gas pressure to the liquid in order to force the liquid from the vessel,
    an orifice means connected to the vessel to permit the liquid to flow from the vessel,
    a valve means connected to said orifice means to control the flow of the liquid, the valve means including a valve block having inlet and outlet orifices, a ball mounted on a shaft with the shaft rotatably mounted in said valve block, said ball having a bore therethrough, pivot means to rotatably mount the shaft in said valve block, automatic remote control means to selectively turn the shaft in order to operate the valve means by aligning its bore with the inlet and outlet orifices of the valve block, and means to measure the weight of the said liquid which flows through said valve means in a predetermined time period.

2. A viscometer system as in claim 1 and further including, as the means to weigh said liquid, a load cell and a container attached to a load cell to receive and weigh the liquid.

3. A viscometer system as in claim 1 and further including computer program command means to operate said control means under control of a digital computer program.

4. A viscometer system as in claim 1 and further including, as portions of said control means: a pneumatic cylinder and piston, a pneumatic valve connected to and controlling said pneumatic cylinder, and said system further including a programmed digital computer connected to and controlling said pneumatic valve.

5. A viscometer system as in claim 1 wherein said pressure means includes a cylinder of pressurized gas and a gas pressure regulator valve.

* * * * *